United States Patent
Öffner

(10) Patent No.: US 10,037,043 B2
(45) Date of Patent: Jul. 31, 2018

(54) APPARATUS FOR PROVIDING A GAS

(71) Applicant: ibidi GmbH, Martinsried (DE)

(72) Inventor: Wolfgang Öffner, Plankstadt (DE)

(73) Assignee: IBIDI GMBH, Martinsried (DE)

( * ) Notice: Subject to any disclaimer, the term of this patent is extended or adjusted under 35 U.S.C. 154(b) by 0 days.

(21) Appl. No.: 14/182,020

(22) Filed: Feb. 17, 2014

(65) Prior Publication Data

US 2014/0238496 A1  Aug. 28, 2014

(30) Foreign Application Priority Data

Feb. 26, 2013 (EP) .................................... 13156779

(51) Int. Cl.
| | | |
|---|---|---|
| *C12M 1/00* | (2006.01) | |
| *G05D 22/00* | (2006.01) | |
| *C12M 1/02* | (2006.01) | |
| *C12M 1/34* | (2006.01) | |

(52) U.S. Cl.
CPC ............. *G05D 22/00* (2013.01); *C12M 29/26* (2013.01); *C12M 41/14* (2013.01); *C12M 41/20* (2013.01); *C12M 41/34* (2013.01); *Y10T 137/0318* (2015.04); *Y10T 137/2499* (2015.04)

(58) Field of Classification Search
CPC ......... Y10T 137/2499; Y10T 137/2501; Y10T 137/87338; C12M 41/14; C12M 29/26; C12M 41/12; C12M 41/32
USPC ...................... 261/45, 129, 63, 119.1, 121.1; 128/203.25
See application file for complete search history.

(56) References Cited

U.S. PATENT DOCUMENTS

| | | | | |
|---|---|---|---|---|
| 3,158,154 A | * | 11/1964 | Schreiber .............. | A61M 16/18 128/203.25 |
| 3,588,057 A | * | 6/1971 | Breiling ................ | A61M 16/18 128/203.25 |
| 4,474,537 A | * | 10/1984 | Dolz ...................... | F04B 35/045 310/35 |
| 5,500,027 A | * | 3/1996 | Rudolph ................. | B01F 3/06 261/22 |
| 6,271,188 B1 | * | 8/2001 | Eschwey et al. ............ | 510/175 |
| 6,896,247 B2 | * | 5/2005 | Brotzeller et al. ............ | 261/128 |
| 7,438,079 B2 | * | 10/2008 | Cohen et al. ...................... | 137/3 |
| 7,992,843 B2 | * | 8/2011 | Reichert ............... | A61M 16/18 128/203.25 |
| 2007/0018344 A1 | * | 1/2007 | Mueller et al. ............... | 261/131 |
| 2012/0122201 A1 | * | 5/2012 | Butler et al. ............... | 435/303.1 |
| 2012/0220026 A1 | * | 8/2012 | Okusa et al. ............... | 435/289.1 |

FOREIGN PATENT DOCUMENTS

WO  WO 0113981 A1 * 3/2001 ............ A61M 16/16

* cited by examiner

*Primary Examiner* — Kevin Murphy
(74) *Attorney, Agent, or Firm* — Moore & Van Allen PLLC; Henry B. Ward, III

(57) ABSTRACT

The application relates to an apparatus for providing a gas for the introduction thereof into an incubation chamber, comprising an inlet port (1) for introducing a gas, an outlet port (2) for discharging a gas, a first gas path (3) connecting the inlet port (1) to the outlet port (2), a second gas path (4) branching off from the first gas path (3) and running back into the first gas path (3); a distributing element (5), configured to allow a portion of the gas introduced through the inlet port (1) to be conducted via the second gas path (4), and an enriching element (6) arranged in the second gas path for enriching the gas flow with a liquid.

15 Claims, 3 Drawing Sheets

APPARATUS FOR PROVIDING A GAS

FIELD OF THE INVENTION

The present application relates to an apparatus for providing a gas for the introduction thereof into an incubation chamber.

BACKGROUND OF THE INVENTION

If it is desired, for instance, to incubate living cells in a medium over a longer period it is important to be capable of adjusting the atmosphere parameters in the incubation chamber with exactness. Cells are, for instance, frequently cultivated in small containers that are filled with an aqueous medium. An evaporation of the aqueous medium results in changed concentrations in the medium which, again, may have the result that the cells die off. Therefore, in order to prevent this evaporation and desiccation, there is a need for the ability to control the humidity, in particular to adjust a high relative gas humidity, respectively air humidity.

In the prior art various methods are known to achieve such a humidity control.

According to a first alternative atomizers are applied which inject atomized liquid into the gas volume. The small water drops are absorbed by the gas which is unsaturated with water. The gas humidity is controlled by the amount of injected liquid. A reduction of the gas humidity can only be obtained by the gas exchange to the environment.

It is a drawback of an atomizer, however, that the gas mixture at the nozzle outlet of this atomizer is supersaturated, which may lead to a condensation and corrosion. Moreover, the humidity of the gas volume has to be less than 100% to allow the absorption of the injected amount of water. Consequently, portions of the gas volume have relative humidities of less than 100%, and the gas in the proximity of the nozzle is supersaturated. Such gradients in the gas volume are not desirable, however. In order to reduce the humidity it is furthermore required to open the incubation chamber. Eventually, the temperature of the gas at the atomizer falls to a great extent owing to the evaporation energy, and this leads to undesired temperature gradients in the gas, too.

One alternative solution is an evaporator, which conventionally comprises a container with water which is mounted in the gas volume. The liquid in the container evaporates and humidifies the gas until an equilibrium has been obtained. This equilibrium corresponds to the saturation concentration. As long as the amount of water is enough and the water surface is correspondingly large it will always be possible to obtain an equilibrium in this way.

A disadvantage is the inertia of this system, however, because the system requires a certain period of time until an equilibrium is established. Although the evaporation of the liquid can be accelerated by increasing the temperature, this process, too, is not very fast. If a system is used that requires a gas exchange, achieving the saturation concentration is no longer ensured. Finally, also the open water surface in the gas volume represents a drawback, e.g. in moving applications or applications replete with vibrations.

Finally, it is also known to use gas washing bottles for humidifying the gas. In this case, dry gas is conducted through a liquid so as to humidify the gas. This humidification happens fast as gas bubbles form a large surface with the water. The humid gas mixture can than be conducted into the occluded gas volume of the incubation chamber. The relative humidity in the gas volume in the incubation chamber can then be controlled by the liquid absorbed by and transported in the gas. The amount of liquid absorbed by the gas can be controlled by the water bath temperature as the absorption capacity of the gas is temperature-dependent. A reduction of the humidity, again, requires a gas exchange in the volume, i.e. the incubation chamber has to be opened.

This system allows a fast humidification of the gas. To allow the controlling of the humidity in a small gas flow it is necessary, however, that plenty of humidity is transported in the inflowing gas. This is usually accomplished by adjusting the temperature of the liquid bath through which the dry gas is conducted. Thus, the inflowing gas is heated, and the absorption of liquid is increased. Many liquids, e.g. water, have a high heat capacity, however, so that the system becomes quite inert as a fast temperature adjustment is impossible. Thus, it is impossible to control the humidity of the gas volume in the incubation chamber fast enough, and this frequently entails condensation problems if the gas volume is operated near the saturation concentration. Furthermore, it is impossible to go below a certain minimum humidity as the inflowing gas is humidified even if the liquid bath of the gas washing bottle is not heated. The control range is typically between 60% and 100% of the relative gas humidity.

BRIEF SUMMARY OF THE INVENTION

Thus, it is the object of the present invention to provide an apparatus which allows the liquid portion of a gas to be controlled fast and flexibly. This object is achieved by an apparatus according to claim 1.

The apparatus according to the invention for providing a gas for the introduction thereof into an incubation chamber comprises:

an inlet port for introducing a gas, an outlet port for discharging a gas, a first gas path connecting the inlet port to the outlet port;

a second gas path branching off from the first gas path and running back into the first gas path;

a distributing element configured to allow a portion of the gas introduced through the inlet port to be conducted via the second gas path; and an enriching element arranged in the second gas path for enriching the gas flow with a liquid.

This apparatus allows that an adjustable portion of a gas is conducted via the second gas path and is enriched with a liquid by the enriching element. This enriched gas can then be mixed with the gas remaining in the first gas path. Thus, a gas can be provided that has an adjustable portion of liquid.

It has shown that the humidity, i.e. the liquid portion of a gas, can be controlled very fast by means of such a system. The control time is determined by the gas flow rate, and not by the inertia of the liquid bath temperature control as in known prior art systems. In addition, the humidity can be controlled between 0% and 100% by conducting a respective portion via the second gas path.

In particular, the liquid used for enriching the gas may be water, in this case, the portion of water vapor in the gas is to be controlled in open or closed loop it is also conceivable, however, to use ethanol or toluol as liquid. Also, the liquid may be a combination of several liquids.

In particular, the gas may be air, that is, where applicable, compressed atmosphere air. It is also possible to use a gas having a minimized reaction, e.g. nitrogen or argon, or a reactive gas, e.g. oxygen, instead of air. The gas may also be an optional mixture of different gases.

In particular, the apparatus may serve to provide a gas with an adjustable liquid portion.

A gas having a specific liquid portion may be a gas having a specific gas humidity or humidity. The liquid is then provided in the gas in the form of a liquid vapor, e.g. water vapor. The gas humidity may be specified as relative gas humidity, i.e. as a ratio of the actually contained to the maximally possible liquid mass in a certain gas volume. If water is used as liquid, and air as gas, the air humidity is, in particular, one that can be specified as relative air humidity.

In particular, the inlet port of the apparatus may be provided to introduce a dry gas. Dry gas refers to a gas that has substantially no liquid portion, that is, whose relative gas humidity is 0%.

The gas path denotes herein in particular a fluidic connection between two points, i.e. a path on which a gas flow is, in principle, possible. A gas path may be formed or defined, for instance, by a gas conduit, e.g. in the form of a pipe or hose.

In particular, the second gas path may be a bypass line to the first gas path. Hence, it may be possible by means of the second gas path to bypass at least a portion of the introduced gas past at least a part of the first gas path.

This means that the second gas path may branch off from the first gas path at a first point and run back into the first gas path at a second, different point.

In particular, the gas portion that can be conducted via the second gas path may be adjustable. In particular, the distributing element may be configured such that the portion that can be conducted via the second gas path is adjustable. The portion may be adjustable between 0% and 100%. In other words, the distributing element may be configured such that the total gas introduced through the inlet port flows via the first gas path in a first adjustment, or that the total inflowing gas is conducted via the second gas path in another adjustment, or that an adjustable portion unequal to 0 is conducted via the first gas path and an adjustable portion unequal to 0 is conducted via the second gas path according to yet other adjustments.

The first gas path may be configured to be flown through by a gas from the inlet port up to the orifice of the second gas path without an increase of the gas humidity of the gas. In other words, it is possible that no enriching element for enriching the gas flow with a liquid is arranged in the first gas path between the inlet port and the orifice of the second gas path. Thus, it is possible to mix the gas enriched with a liquid and flowing out of the second gas path into the first gas path with a gas that has a predetermined gas humidity, e.g. with dry gas.

In the region where the second gas path runs into the first gas path a mixing chamber may be arranged, which is configured to agitate the gas from the first gas path and the gas from the second gas path in a directed manner. This allows a better mixing of the gases.

The first gas path may furthermore be configured such that no enriching element for enriching a gas with a liquid is located between the orifice of the second gas path into the first gas path and the outlet port either. Thus, it is possible to keep the gas humidity obtained by mixing the gases from the second gas path and the front portion of the first gas path constant and supply it to an incubation chamber.

In particular, the distributing element may be controllable in open-loop or closed-loop. In other words, the gas portion conducted via the second gas path may be controllable in open-loop or closed-loop. Thus, it is possible to control the gas humidity between 0% and 100%. In particular, the controlling in open-loop or closed-loop may be based on an adjustable gas humidity to be achieved. For instance, if dry gas, i.e. gas having a 0% gas humidity, is to be conducted into the incubation chamber, the portion of the gas to be conducted via the second gas path is 0. In other words, the distributing element is configured to conduct, in this case, the total introduced gas via the first gas path.

However, if a relative gas humidity of 100% is desired the portion of the gas to be conducted via the second gas path is 100%. In other words, the total gas introduced through the inlet port is conducted via the second gas path.

For gas humidities there between the portion of the gas conducted via the second gas path may be determined correspondingly. The controlling of the distributing element in open-loop or closed-loop may be accomplished by a control element of the apparatus, e.g. in the form of a microcontroller.

The apparatus may furthermore comprise a sensor for determining the liquid portion of a gas, which is arranged in the first gas path, downstream of the orifice of the second gas path into the first gas path, or can be arranged in an incubation chamber, wherein the distributing element can be controlled on the basis of a measurement of the sensor. In particular, the portion of the gas conducted via the second gas path may be controllable on the basis of the humidity measurement of the sensor. Such a sensor allows a simple adjustment of the desired gas humidity.

The apparatus may furthermore comprise a temperature sensor for determining the temperature of a gas, which is arranged in the first gas path, downstream of the orifice of the second gas path into the first gas path, or can be arranged in an incubation chamber, wherein the distributing element can be controlled on the basis of a temperature measurement of the temperature sensor. Thus, the control can be further improved as the relative gas humidity is temperature-dependent.

In particular, the above-mentioned sensors may be arrangeable in the gas volume of the incubation chamber. Also, additional sensors of this type may be provided between the orifice of the second gas path into the first gas path and an incubation chamber.

In particular, the above-mentioned sensors may be connected to a control device of the apparatus, which controls in open-loop or closed-loop the distributing element.

The enriching element may comprise a container for a liquid. The apparatus may be configured such that a liquid, which can be arranged in the container, can be flown through by a gas conducted via the second gas path. In particular, the enriching element can comprise or can be at least one, in particular heatable gas washing bottle. In particular, if several liquids are to be combined with one another several containers, in particular gas washing bottles, may be provided which are each filled with a desired liquid. In this case, the gas can flow in the second gas path sequentially through the individual containers, in particular gas washing bottles. Hence, the containers may be arranged one after the other or in series.

In particular, the distributing element may be a mixing valve. A mixing valve allows the simple controlling in open-loop or closed-loop of the portion of the introduced gas conducted via the second gas path.

A flow meter may be arranged upstream and/or downstream of the distributing element. This flow meter may be used to control the distributing element.

The inlet port may comprise a connection for at least one gas bottle containing a precompressed gas. Alternatively, or in addition thereto, the apparatus may comprise a compressor connected to the inlet port and/or a pump connected to the inlet port. Thus, it is possible to provide a gas with a predetermined pressure at the inlet port.

The apparatus may furthermore comprise a mixing device for mixing different gases, which is connected to the inlet port. In this case, the gas can correspond to a gas mixture.

The mixing device may be connected to several devices for providing a gas, e.g. in the form of gas bottles, wherein each device for providing a gas is assigned a flow valve with an adjustable opening. Downstream of at least one valve, in particular of all valves, a flow meter may be positioned. The gases coming from the devices for providing a gas may be mixed to a gas mixture in the mixing device. The mixing device may comprise a gas concentration sensor. The gas concentration sensor is capable of checking the mixing ratio of the gases. Based on the measurement of the gas concentration sensor the flow valves may be controlled by a corresponding feedback control so that the concentrations in the gas mixture correspond to the desired concentrations. Correspondingly, at least one humidity sensor may be provided for controlling the humidity of the gas mixture. In this case, the devices for providing a gas may be configured to provide gases with different gas humidities.

In particular, the above-mentioned pump may be an oscillating pump or magnetic piston pump whose performance is, in particular, controlled by rectangular pulses of varying lengths. Thus, it is possible to significantly simplify the control electronics. In particular, the digital signals required for the controlling can be generated by a timing generator of a microcontroller used for controlling the distributing element. The signals may furthermore be amplified by a H-bridge. In addition, a capacitor may be connected in series with the oscillating pump, which forms a series resonant circuit with the pump inductance. Thus, the voltage at the pump may have a sinusoidal shape.

In addition, the invention provides a system comprising an above-mentioned apparatus and an incubation chamber, wherein the incubation chamber is connected by a gas conduit to the outlet port of the apparatus. Such a system allows to control the gas humidity in a gas volume of the incubation chamber in a simple and fast manner.

In particular, the apparatus may include one or more of the above-mentioned features. In particular, the above-mentioned sensors may be arranged in the incubation chamber.

In particular, the incubation chamber may be an incubation chamber for a microfluid apparatus. This means that the incubation chamber may in particular, be an incubation chamber for microbiological applications, e.g. for cultivating living cells.

The gas conduit may comprise at least one, in particular controllable heating hose. Thus, the temperature and, thus, the relative gas humidity can be kept constant on the way from the outlet port to the inlet of the incubation chamber.

It is also possible that several above-described devices, which are connected to the incubation chamber, are provided in the system. They may be arranged in series, meaning one after the other. Thus, several liquids may be combined with one another in a simple way. The devices may also be connected in parallel, meaning independently of one another, to the incubation chamber. Thus, it is possible to provide different atmospheres in the incubation chamber in a fast and flexible way.

In addition, the invention provides a method for providing a gas for the introduction thereof into an incubation chamber, comprising the steps of:
  introducing a gas into a first gas path;
  conducting a portion of the gas via a second gas path, which branches off from the first gas path and runs back into the first gas path;
  enriching the gas in the second gas path with a liquid by means of an enriching element arranged in the second gas path, and
  passing the liquid-enriched gas on into the first gas path.

Such a method allows to control the gas humidity in a gas volume of an incubation chamber fast and exactly.

In particular, the method may comprise an introduction of a gas with an adjustable liquid portion into the incubation chamber. In other words, the method may be used for controlling in open-loop or closed-loop a gas humidity in an incubation chamber.

In particular, the liquid, the gas, the incubation chamber and/or the liquid paths may include one or more of the above-mentioned features. In particular, the method may comprise providing an above-described system or an above-described apparatus, wherein the apparatus or the system are used for the method steps.

Thus, the invention also provides a use of an above-described system or an above-described apparatus for controlling in open-loop or closed-loop the gas humidity in a gas volume of an incubation chamber.

In the above-mentioned method the portion of the gas to be conducted via the second gas path may be between 0% and 100%. That is, the portion may in particular be adjustable. If the portion is 0% the steps of conducting the portion via the second gas path, of enriching the gas, and of conducting it back into the first gas path are not carried out. In other words, if a gas with an original liquid portion is to be provided, in particular dry gas, the method may comprise conducting the total gas from the inlet port to the outlet port on the first gas path.

If the portion amounts to 100% the gas is conducted only via the second gas path. In this case, no mixing with gas remaining in the first gas path takes place.

In particular, the gas introduced into the first gas path may be dry gas.

In particular, the second gas path may branch off from the first gas path at one point and run back into the first gas path at another point.

The introduction of the gas into the first gas path may comprise controlling an input pressure. The pressure control may be accomplished by means of an oscillating pump, wherein the oscillation amplitude and, thus, the performance of the oscillating pump is controlled by rectangular pulses of varying lengths.

In particular, the introduced gas may correspond to a gas mixture. In this case, gases may be mixed prior to the introduction of the gas. This mixing may be carried out by means of several devices for providing a gas, wherein each device for providing a gas is assigned a flow valve, wherein a flow meter is positioned downstream of at least one valve, in particular downstream of all valves, the flow meter measuring the flow through each valve. The gases coming from the devices for providing a gas may be mixed to one gas or a gas mixture in a mixing section of a mixing device. The mixing ratio of the gases may be checked by a gas concentration sensor. Based on the measurement of the gas concentration sensor the flow valves may be controlled by a corresponding feedback control so that the concentrations in the gas mixture correspond to the desired concentrations.

BRIEF DESCRIPTION OF THE DRAWINGS

Other features and advantages of the invention will be explained below by means of the exemplary figures. In the figures.

DETAILED DESCRIPTION OF THE INVENTION

Below, it will be assumed on an exemplary basis that the introduced gas is a mixture of $CO_2$ and air, which is to be enriched with a liquid. The liquid is water. It will be appreciated, however, that the invention is not limited to this specific example. Another possible liquid would be, for instance, alcohol or toluol. Also, instead of air and $CO_2$ (carbon dioxide), a gas having a minimized reaction or a reactive gas may be used. Optional gas mixtures are conceivable, too.

Figure 1:
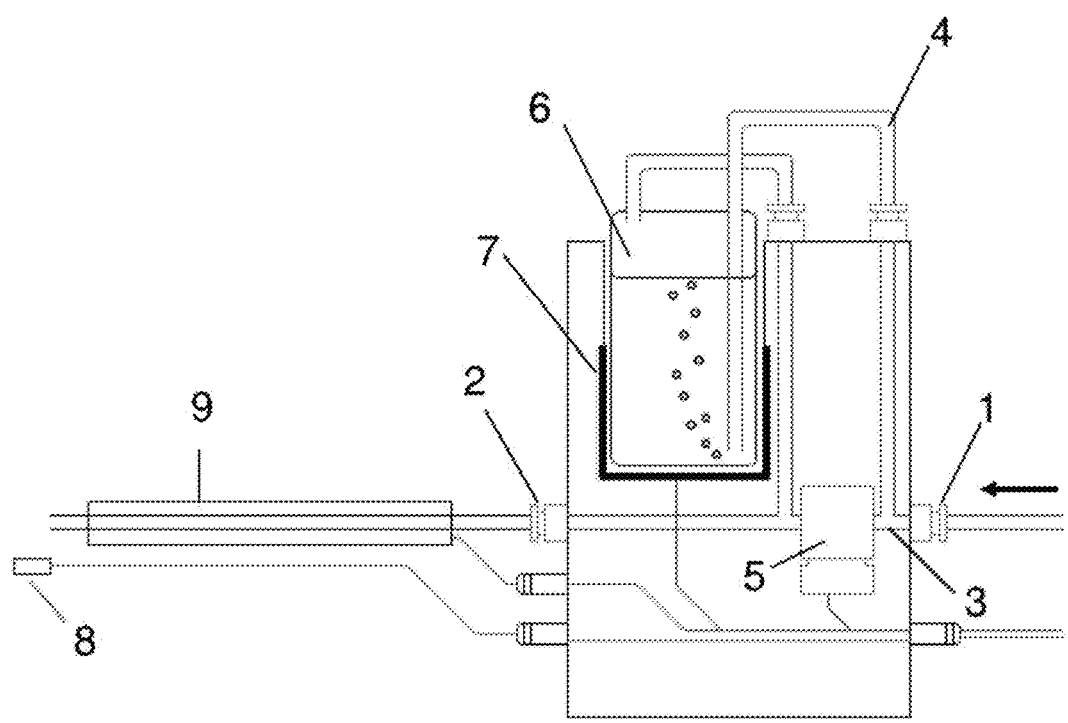
FIG. 1 shows the schematic structure of an exemplary apparatus for providing a gas.

FIG. 1 shows an exemplary apparatus for providing a gas with an adjustable liquid portion for the introduction thereof into an incubation chamber. The apparatus comprises an inlet port 1 for introducing a gas, in particular a dry gas, an outlet port 2 for discharging a gas, and a first gas path 3 connecting the inlet port 1 to the outlet port 2. A second gas path 4 branches off from the first gas path 3 at a first point and runs back into the first gas path 3 at a second, different point. By means of a distributing element 5, which may be configured, for instance, as a mixing valve controllable in open-loop or closed-loop, it is possible to conduct an adjustable portion of the introduced gas via the second gas path 4.

An enriching element configured as a gas washing bottle 6 is arranged in the second gas path. This element may humidify the flowing gas with a liquid, in this example water. The gas washing bottle 6 can be temperature-controlled by a controllable heater 7. Other enriching elements are conceivable, too, as the enriching element. For instance, alternatively or additionally, one or more atomizers may be used as enriching element.

A controllable heating hose 9 is connected to the outlet port 2, by means of which the humidity-controlled gas can be conducted to an incubation chamber (not illustrated). FIG. 1 additionally shows a temperature and/or humidity sensor 8 which, for instance, may be arranged in the incubation chamber. Based on the measurements of this sensor 8, for instance, the distributing element 5, the heating element 7 and/or the heating hose 9 can be controlled.

This apparatus can be used, for instance, for the humidity control in an incubation chamber for living cell microscopy. In particular, the incubation chamber may be an incubation chamber for microfluid apparatus. The incubation chamber may have such a size that exactly one microfluid apparatus can be arranged in the incubation chamber.

In the application, an inflowing $CO_2$-controlled dry gas mixture is to be humidified such that the small amounts of water in the sample chambers in the incubation chamber, in which the cells are cultivated, do not evaporate. Only thus can long test periods be realized without having to open the incubation chamber.

Initially, dry gas, e.g. pure $CO_2$ and air, is mixed and compressed in a gas source (not illustrated) connected to the inlet port 1. The gas mixture is then conducted through the inlet port 1 into the apparatus. In the apparatus there are two paths for the gas. The second gas path 4 leads through the gas washing bottle 6 containing a temperature-controlled water bath. This path has a higher flow resistance. The other, first gas path 3 bypasses the gas washing bottle 6 and has a lower flow resistance.

The amount of gas bypassing the water bath may be controlled by the mixing valve 5. If the mixing valve 5 is completely closed the total gas is passed through the gas washing bottle 6, and is humidified. In this case, the relative humidity of the gas provided by the apparatus amounts to 100% at water temperature. If, on the other hand, the valve 5 is completely opened only dry gas flows out of the apparatus because the gas flow in the first gas path 3 has a lower resistance than in the second gas path 4. The humidity of the gas mixture may be controlled depending on the intermediate position of the mixing valve 5. The humidity sensor 8 in the incubation chamber represents the feedback of this control system.

The position of the mixing valve 5 may also be used for optimizing the water temperature. Thus, in particular a temperature sensor in the water bath may be waived. Instead, the mixing ratio of the gases from the liquid paths 3, 4 may be analyzed. If, for instance, the water bath in the gas washing bottle 6 is too cold, hardly any dry gas is added. On the other hand, if the water bath is too warm, plenty of dry gas is added.

The humidity control described may be used for any incubation chamber. In particular, the incubation chamber may be an incubation chamber for microbiological applications, e.g. for cultivating living cells.

The humidity control described has the following advantages:

A very fast humidity control is possible. The control time is only determined by the gas flow rate, and no longer by the inertia of the water bath temperature control. A fast valve is able to switch immediately from humid to dry gas, or adopt intermediate positions.

The humidity may be controlled between 0% and 100%.

As the reaction of the control is fast a condensation in the gas volume can be effectively prevented.

The method allows working with a gas that has already absorbed humidity. Unlike the atomizer known from the prior art one is not dependent on the liquid absorption of the gas in the gas volume of the incubation chamber.

Moreover, the apparatus may be constructed to be insusceptible to vibrations. In particular, no exposed liquid surfaces are required in the gas volume of the incubation chamber.

The apparatus may furthermore be operated at a minimum gas flow rate as the water bath temperature in the gas washing bottle may be chosen to be higher than in the prior art, where the temperature of the liquid bath is controlled if a gas washing bottle is used. If the liquid bath temperature is higher, more liquid may be transported in the humid gas. On the other hand, the humidity may also be effectively controlled at very high gas flow rates.

Figure 2:
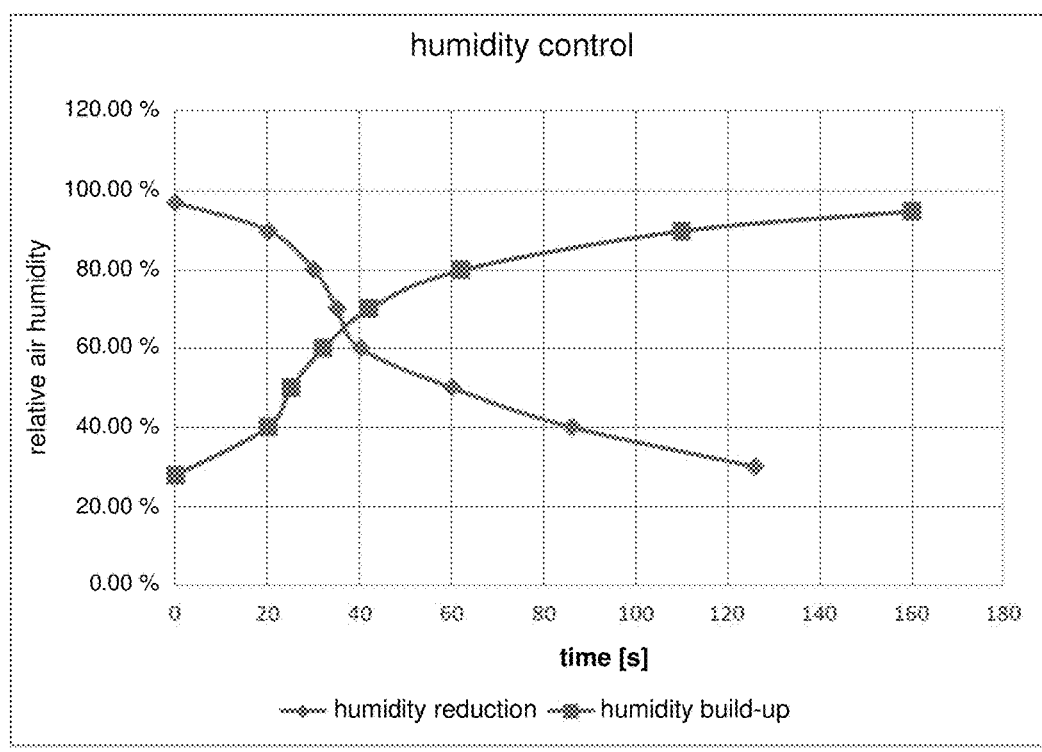
FIG. 2 shows an illustration of the time dependence of a humidity control achievable by means of an exemplary apparatus for providing a gas.

For illustration purposes the experimentally determined course of the humidity reduction, respectively humidity build-up, by means of an above-described exemplary apparatus is shown in FIG. 2. As can be seen by the curves it is possible to control the relative air humidity of the provided gas within a shortest period. The humidity build-up is shown by squares, the liquid reduction by checks.

In FIG. 1 an exemplary system having only one gas washing bottle was shown. Of course, it would also be possible to combine several liquids by using several gas washing bottles connected in series, which are each filled with a different liquid, if necessary.

As was described above, for instance, compressed gas is passed through the inlet port 1. The pressure may be generated by precompressed gas bottles, i.e. pressure reservoirs, or by compressors, respectively pumps. The flow may be controlled by a fine pressure control, by driving the compressors, respectively pressure pumps.

The apparatus may comprise, for instance, an oscillating pump, wherein the oscillating amplitude and, thus, the performance of the pump is controlled by rectangular pulses of varying lengths. In the normal case the pump performance of oscillating pumps is realized by a sinusoidal voltage or a square wave voltage from an inverter. The performance control is then accomplished by control valves, or by changing the alternating voltage amplitude. The advantage of the herein proposed rectangular pulses of varying lengths is that the electronic driving system can be significantly simplified. In particular, the necessary digital signals may simply be generated by a suitable timing generator of the microcontroller, which is provided anyway and controls in open-loop or closed-loop, for instance, the distributing element 5 or the heating element 7, and amplified, for instance, by a H-bridge.

Figure 3:
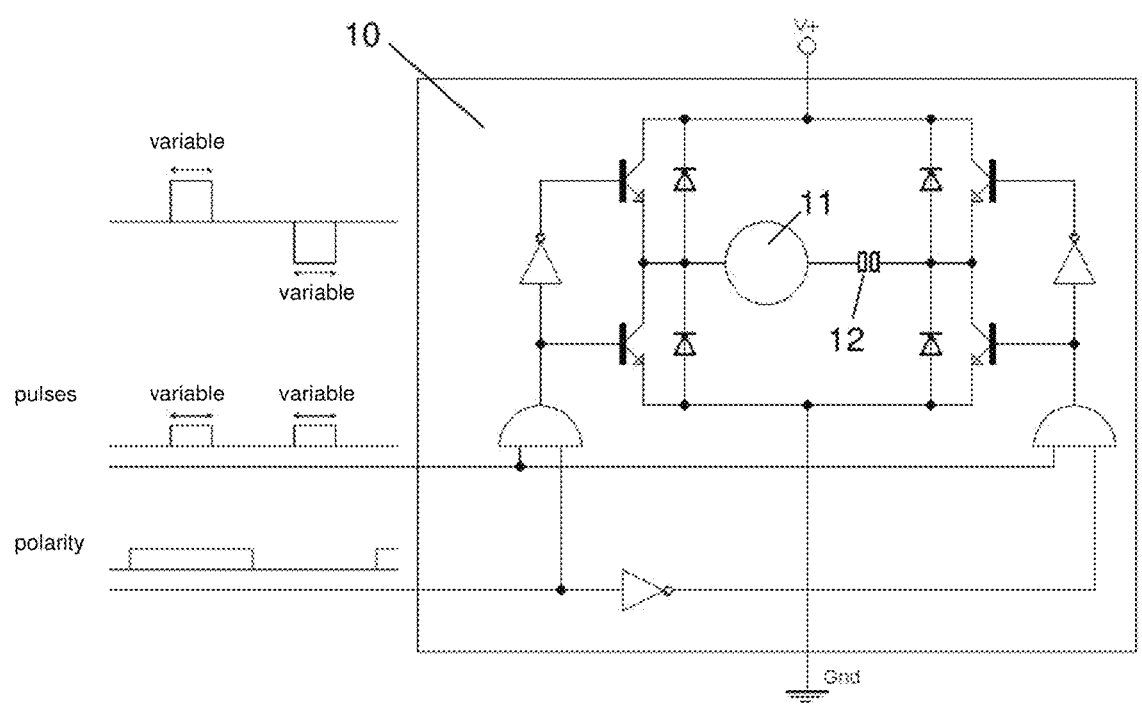
FIG. 3 shows an illustration of a possible controller for controlling a pressure of a gas to be introduced at an inlet port of an exemplary apparatus for providing a gas.

A schematic representation of a corresponding control circuit is shown in FIG. 3. In particular, an integrated H-bridge 10 is schematically illustrated in this figure, integrated H-bridges are available on the market so that only a few components are required to build up this controller. A capacitor 12 connected in series with the oscillating pump 11 forms a series resonant circuit with the pump inductance, so that the voltage at the pump 11 has a sinusoidal shape. The rectangular pulses of varying lengths are also schematically illustrated in FIG. 3. FIG. 3 shows, in particular, the input pulses with a corresponding polarity, and the voltage curve at the output of the H-bridge on top thereof.

It will be appreciated that features recited in the above-described embodiments are not limited to these specific combinations, and are possible in any other optional combinations.

The invention claimed is:

1. Apparatus for providing a gas for the introduction thereof into an incubation chamber having a sample chamber for cultivating living cells, comprising:
   an inlet port for introducing a gas;
   an outlet port for discharging a humidity-controlled gas into the incubation chamber;
   a first gas path connecting the inlet port to the outlet port;
   a second gas path branching off from the first gas path at a first point and running back into the first gas path at a second point;
   a distributing element for allowing a portion of the gas introduced through the inlet port to be conducted via the second gas path;
   an enriching element arranged in the second gas path for enriching the gas flow with water vapor, wherein the enriching element comprises a controllable heating element and a gas washing bottle containing a temperature-controlled water bath, wherein the water bath is temperature controlled by the controllable heating element;
   a controllable heating hose connected to the outlet port and configured to conduct the humidity-controlled gas to the incubation chamber;
   at least one of a temperature sensor and a humidity sensor arranged in the incubation chamber, wherein the distributing element and at least one of (i) the enriching element and (ii) the controllable heating hose, are controllable based on a measurement of the temperature sensor or the humidity sensor;
   wherein the humidity-controlled gas is controlled such that water in the sample chamber in the incubation chamber, in which the living cells are cultivated, does not evaporate;
   wherein (i) the distributing element includes an adjustable valve arranged only along the first gas path between the first point and the second point, wherein the valve is configured such that a size of an opening of the valve is variably adjustable to allow a selected portion of the gas introduced through the inlet port to be conducted via the opening and the first gas path while a remaining portion of the gas introduced through the inlet port is conducted via the second gas path, (ii) a first length of the second gas path between the first point and the enriching element does not include a further valve, and (iii) a second length of the second gas path between the enriching element and the second point does not include a further valve.

2. Apparatus according to claim 1, wherein no enriching element for enriching the gas flow with water vapor is arranged in the first gas path between the inlet port and an orifice of the second gas path.

3. Apparatus according to claim 1, wherein the distributing element is controllable in open-loop or closed-loop.

4. Apparatus according to claim 1, further comprising a sensor for determining the water vapor portion of a gas, which is arranged in the first gas path, downstream of an orifice of the second gas path into the first gas path at the second point, wherein the distributing element is controlled on the basis of a measurement of the sensor.

5. Apparatus according to claim 1, further comprising a temperature sensor, which is arranged in the first gas path, downstream of an orifice of the second gas path into the first gas path at the second point, and wherein the distributing element is controlled on the basis of a measurement of the sensor.

6. Apparatus according to claim 1, wherein the inlet port comprises a connection for at least one gas bottle containing a precompressed gas, or wherein the apparatus comprises a compressor connected to the inlet port and/or a pump connected to the inlet port.

7. Apparatus according to claim 6, further comprising a mixing device for mixing different gases, which is connected to the inlet port.

8. Apparatus according to claim 6, wherein the pump is an oscillating pump.

9. Apparatus according to claim 8, further comprising a timing generator that provides rectangular pulses of varying duration, wherein the oscillating pump is configured to be controlled by the rectangular pulses.

10. Apparatus according to claim 1, wherein the gas washing bottle is a heatable gas washing bottle.

11. Apparatus according to claim 1, wherein the valve is configured such that the opening is adjustable to vary between a substantially closed position and a substantially open position.

12. Apparatus according to claim 1, wherein the controllable heating element is configured to adjust a temperature of the water bath in the gas washing bottle in accordance with the size of the opening of the valve.

13. Method for providing a gas for the introduction thereof into an incubation chamber having a sample chamber for cultivating living cells, comprising the steps of:
   introducing a gas into a first gas path;

conducting a portion of the gas via a second gas path, which branches off from the first gas path at a first point and runs back into the first gas path at a second point, by using a single valve arranged only along the first gas path;

enriching the gas in the second gas path with water vapor by means of an enriching element arranged in the second gas path, wherein the enriching element comprises a gas washing bottle containing a water bath;

controlling the temperature of the water bath by a controllable heater;

passing the water vapor-enriched gas on into the first gas path;

discharging the water vapor-enriched gas into the incubation chamber by a controllable heating hose connected to the incubation chamber;

controlling a humidity of the gas in the incubation chamber such that water in the sample chamber of the incubation chamber, in which the living cells are cultivated, does not evaporate;

controlling the valve and at least one of (i) the enriching element and (ii) the controllable heating hose based on a measurement received at least one of a temperature sensor and humidity sensor arranged in the incubation chamber; and wherein (i) the valve is arranged between the first point and the second point and is configured such that a size of an opening of the valve is variably adjustable to allow a selected portion of the gas introduced through an inlet port to be conducted via the opening and the first gas path while a remaining portion of the gas introduced through the inlet port is conducted via the second gas path, (ii) a first length of the second gas path between the first point and the enriching element does not include a further valve, and (iii) a second length of the second gas path between the enriching element and the second point does not include a further valve.

14. Method according to claim 13, wherein the valve is configured such that the opening is adjustable to vary between a substantially closed position and a substantially open position.

15. Method according to claim 13, further comprising optimizing a temperature of water in the enriching element by adjusting the size of the opening of the valve.

* * * * *